United States Patent [19]

Wong

[11] 4,406,692
[45] Sep. 27, 1983

[54] META-SUBSTITUTED DIALKYLAMINOOXANILIDE POST-EMERGENT HERBICIDES

[75] Inventor: Rayman Y. Wong, Richmond, Calif.

[73] Assignee: Stauffer Chemical Company, Westport, Conn.

[21] Appl. No.: 251,408

[22] Filed: Apr. 6, 1981

[51] Int. Cl.$^3$ .................... A01N 37/18; A01N 47/30; C07C 127/17; C07C 103/24

[52] U.S. Cl. ........................................ 71/120; 71/118; 260/453 RW; 564/50; 564/153

[58] Field of Search ................................ 71/118, 120; 260/453 RW; 564/50, 155, 153, 152

[56] References Cited

U.S. PATENT DOCUMENTS 4,293,331 10/1981 Beck et al. ........................... 71/118

FOREIGN PATENT DOCUMENTS 48-24730 7/1973 Japan.

Primary Examiner—Catherine L. Mills
Attorney, Agent, or Firm—Paul R. Martin

[57] ABSTRACT

Post-emergent herbicides having the formula t,10 wherein

R is alkyl having 1–4 carbon atoms, inclusive; or alkenyl having 2–4 carbon atoms, inclusive; and X is selected from the group consisting of alkyl having 1–4 carbon atoms, inclusive; cycloalkyl having 3–6 carbon atoms, inclusive; dialkylamine wherein the alkyl groups each have 1–4 carbon atoms, inclusive; and N-alkyl-N-alkoxyamine wherein the alkyl and alkoxy groups each have 1–4 carbon atoms, inclusive.

27 Claims, No Drawings

META-SUBSTITUTED DIALKYLAMINOOXANILIDE POST-EMERGENT HERBICIDES

FIELD OF THE INVENTION

This invention relates to post-emergent herbicides, and more particularly, to meta-substituted dialkylaminooxanilide compounds which are useful as post-emergent herbicides.

BACKGROUND OF THE INVENTION

An herbicide is a compound which controls or modifies plant growth. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs.

The most popular methods of herbicide application include: pre-plant incorporation into the soil; in-furrow application to seeds and surrounding soil; pre-emergence surface treatment of seeded soil; and post-emergence treatment of the plant and soil.

A manufacturer of an herbicide generally recommends a range of application rates and concentrations calculated to maximize weed control. The range of rates varies from approximately 0.01 to 50 pounds per acre (0.0112 to 56 kilograms per hectare (k/ha)), and is usually in the range of from 0.1 to 25 pounds per acre (0.112 to 28 k/ha). The term "herbicidally effective amount" describes the amount of an herbicide compound which controls or modifies plant growth. The actual amount used depends upon several consideration, including particular weed susceptibility and overall cost limitations.

DESCRIPTION OF THE INVENTION

It has now been discovered that certain meta-substituted-dialkylaminooxanilides are effective post-emergent herbicides for the control or modification of plant growth. These compounds have the general formula:

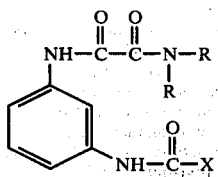

wherein
R is alkyl having 1-4 carbon atoms, inclusive; or alkenyl having 2-4 carbon atoms, inclusive; and
X is selected from the group consisting of alkyl having 1-4 carbon atoms, inclusive; cycloalkyl having 3-6 carbon atoms, inclusive; dialkylamine wherein the alkyl groups each have 1-4 carbon atoms, inclusive; and N-alkyl-N-alkoxyamine wherein the alkyl and alkoxy groups each have 1-4 carbon atoms, inclusive.

All carbon ranges are inclusive of both upper and lower limits. Exemplary of alkyl are methyl, ethyl, n-propyl, isopropyl and the like; exemplary of alkenyl are ethene, propene and the like; exemplary of alkoxy are methoxy, ethoxy, and the like.

In a preferred embodiment, R is selected from the group consisting of methyl, ethyl, n-propyl, and 1-propene, and X is selected from the group consisting of ethyl, cyclopropyl, dimethylamine and N-methyl-N-methoxy amine.

This invention also embodies a method of controlling or modifying plant growth which comprises applying to the locus where control or modification is desired a compound of the formula:

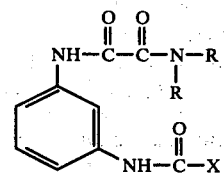

wherein
R is alkyl having 1-4 carbon atoms, inclusive; or alkenyl having 2-4 carbon atoms, inclusive;
X is selected from the group consisting of alkyl having 1-4 carbon atoms, inclusive; cycloalkyl having 3-6 carbon atoms, inclusive; dialkylamine wherein the alkyl groups each have 1-4 carbon atoms, inclusive; and N-alkyl-N-alkoxyamine wherein the alkyl and alkoxy groups each have 1-4 carbon atoms, inclusive.

The locus where control or modification is desired may include soil, seeds, seedlings, or vegetation.

Preparation

The meta-substituted-dialkylaminooxanilide compounds of this invention can be prepared according to the following general procedure, depending on the starting materials. Meta-substituted ethylthiooxanilide is reacted with an appropriate dialkylamine in a suitable solvent. Suitable solvents may include such standard organic reagents as tetrahydrofuran and dichloromethane. After continuous stirring at room temperature the meta-substituted dialkylaminooxanilide may be washed, dried, filtered and stripped. Structure may be confirmed by infrared (IR), nuclear magnetic resonance (NMR), or mass (MS) spectroscopy.

The following examples illustrate the preparation of specific compounds according to this general method. (Compound numbers correspond to those in Tables I, III, IV, and V).

EXAMPLE I (Compound No. 1)

Preparation of Meta-substituted-(N,N-dimethylureido)-dimethylaminooxanilide

Two grams (g) (6.8 millimole) of m-(N,N-dimethylureido)ethylthiooxanilide were dissolved in 50 milliliters (ml) of dichloromethane and introduced into a reaction flask. One and a half g (34.0 millimole) of dimethylamine were added to the reaction flask. After continuous stirring at room temperature for one hour, the mixture was washed once with hydrochloric acid, once with a saturated sodium carbonate solution, once with water, and once with a saturated sodium chloride solution. The mixture was dried over sodium sulfate, filtered and stripped. Yield was 1.3 g m-(N,N-dimethylureido)dimethylaminooxanilide. (m.p.=75° C.) Structure was confirmed by IR and NMR.

EXAMPLE II (Compound No. 4)

Preparation of Meta-(N,N-dimethylureido)-di-2-propenylaminooxanilide

Two grams (g) (6.8 millimole) of m-(N,N-dimethylureido)ethylthiooxanilide were dissolved in 50 ml of dichloromethane and introduced into a reaction flask. Three and three-tenths g (34.0 millimole) of diallylamine were added to the reaction flask. After continuous stirring at room temperature for 26 hours, the mixture was washed once with hydrochloric acid, once with a saturated sodium carbonate solution, once with water and once with a saturated sodium chloride solution. The mixture was dried over sodium sulfate, filtered and stripped. Yield was 1.8 g m-(N,N-dimethylureido)-di-2-propenylaminooxanilide. (m.p.=49° C.) Structure was confirmed by NMR.

EXAMPLE III (Compound No. 7)

Preparation of Meta-(N-methyl-N-methoxyureido)-di-(1-propyl-)aminooxanilide

Two g (6.7 m-mole) of m-(N,N-dimethylureido)-ethylthiooxanilide were dissolved in 30 ml of dichloromethane and introduced into a reaction flask. Four and four-tenths g (33.5 m-mole) of di-n-propylamine were added to the reaction flask. After continuous stirring at room temperature for 72 hours, the mixture was washed once with hydrochloric acid, once with water and once with a saturated sodium chloride solution. The mixture was dried over sodium sulfate, filtered and stripped. Yield was 2.0 g m-(N-methyl-N-methoxyureido)-di-(1-propyl)aminooxanilide (m.p.=50° C.) Structure was confirmed by IR, NMR, and MS.

EXAMPLE IV (Compound No. 10)

Preparation of Meta-propionamido diethylaminooxanilide

Two and one-half g (9.4 m-mole) of m-(propionamido)-methylthiooxanilide were dissolved in 50 ml of tetrahydrofuran and introduced into a reaction flask. Three and four-tenths g of diethylamine were added to the flask. After continuous stirring at room temperature for 72 hours, the tetrahydrofuran was stripped from the reaction mixture. Dichloromethane was added and the resulting solution was washed once with hydrochloric acid, once with a saturated sodium carbonate solution, once with water, and once with a saturated sodium chloride solution. The mixture was dried over sodium sulfate, filtered and stripped. Yield was 1.5 g of meta-propionamido-diethylaminooxanilide, a yellow waxy solid. Structure was confirmed by IR, NMR, and MS.

The compounds prepared according to these procedures appear in Table I.

TABLE I

Meta-(N,N—Dimethylureido)-dialkylaminooxanilides

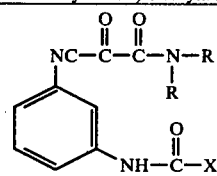

| Cmpd. No. | X | R | Chemical Name | Physical Constant |
|---|---|---|---|---|
| 1 | N(CH3)2 | CH3 | meta-(N,N—dimethylureido)-dimethylaminoxanilide | m.p. ≈ 75° C. |
| 2 | N(CH3)2 | C2H5 | meta-(N,N—dimethylureido)-diethylaminooxanilide | m.p. = 160-163° C. |
| 3 | N(CH3)2 | n-C3H7 | meta-(N,N—dimethylureido)-di-1-propylaminooxanilide | m.p. = 42-44° C. |
| 4 | N(CH3)2 | —CH2CH=CH2 | meta-(N,N—dimethylureido)-di-2-propenylaminooxanilide | m.p. = 48-50° C. |
| 5 | N—CH3 OCH3 | CH3 | meta-(N—methoxy-N—methyl-ureido)-dimethylaminooxanilide | m.p. ≈ 47° C. |
| 6 | N—CH3 OCH3 | C2H5 | meta-(N—methoxy-N—methyl-ureido)-diethylaminooxanilide | m.p. = 57° C. |
| 7 | N—CH3 OCH3 | n-C3H7 | meta-(N—methoxy-N—methyl-ureido)-dipropylaminooxanilide | m.p. = 50° C. |
| 8 | N—CH3 OCH3 | —CH2CH=CH2 | meta-(N—methoxy-N—methyl-ureido)-di-(2-propenyl)-aminooxanilide | glass |
| 9 | C2H5 | CH3 | meta-propionamido-dimethyl-aminooxanilide | m.p. = 40° C. |
| 10 | C2H5 | C2H5 | meta-propionamido-diethyl aminooxanilide | waxy solid |
| 11 | C2H5 | n-C3H7 | meta-propionamido-di-(1-propyl)aminooxanilide | waxy solid |
| 12 | C2H5 | —CH2CH=CH2 | meta-propionamido-di-(2-propenyl)-aminooxanilide | glass |
| 13 | ◁ | CH3 | meta-cyclopropionamido-dimethylaminooxanilide | m.p. = 50° C. |

TABLE I-continued

Meta-(N,N—Dimethylureido)-dialkylaminooxanilides

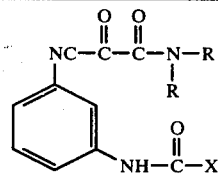

| Cmpd. No. | X | R | Chemical Name | Physical Constant |
|---|---|---|---|---|
| 14 | ◁ | $C_2H_5$ | meta-cyclopropionamido-diethylaminooxanilide | m.p. ≈ 155° C. |
| 15 | ◁ | $n-C_3H_7$ | meta-cyclopropionamido-di-(1-propyl)-aminooxanilide | m.p. = 65° C. |
| 16 | ◁ | $-CH_2CH=CH_2$ | meta-cyclopropionamido-di-(2-propenyl)aminooxanilide | m.p. = 46° C. |

Testing

Sandy loam soil was fortified with 50 parts per million (ppm) each of a commercially available fungicide, cis-n-[(trichloromethyl)thio]-4-cyclohexene-1,2-dicarboximide and 17-17-17 fertilizer, which contains 17% by weight each of nitrogen, phosphorus pentoxide, and potassium oxide. The fortified soil was placed either in fiber flats measuring 15×25×6.5 cm or in aluminum flats measuring 22.9×17.25×7.5 cm. Furrows were impressed across the width of the flats. Seeds were planted in the furrows at a depth of 1.25 cm. Enough seeds are planted to give about 20 to 50 seedlings per row after emergence.

A summary of the species seeded appears in Table II.

TABLE II

| Common Name | Abbreviation | Species Seeded Type | Scientific Name |
|---|---|---|---|
| Annual morningglory | AMG | broadleaf weed | Ipomoea spp. |
| Cocklebur | CB | broadleaf weed | Xanthium spp. |
| Jimsonweed | JW | broadleaf weed | Datura stramonium |
| Velvetleaf | VL | broadleaf weed | Abutilon theophrasti |
| Mustard | MD | broadleaf weed | Brassica spp. |
| Nightshade | NSD | broadleaf weed | Solanum spp. |
| Pigweed | PW | broadleaf weed | Amaranthus retroflexus |
| Downybrome | DB | grass | Bromus tectorum |
| Foxtail | FT | grass | Setaria spp. |
| Annual ryegrass | ARG | grass | Lolium multiflorum |
| Watergrass | WG | grass | Echinochloa crusgalli |
| Shattercane | SHC | grass | Sorghum bicolor |
| Wild Oat | WO | grass | Avena fatua |
| Soybean | SOY | broadleaf crop | Glycine max |
| Rice | RC | grass crop | Oryza sativa |
| Cotton | COT | broadleaf crop | Gossypium hirsutum |
| Corn | CN | grass crop | Zea mays |
| Wheat | WH | grass crop | Triticum aestivum |
| Milo | ML | grass crop | Sorghum vulgare |

The seeded flats were placed in a greenhouse at a temperature of 70°-80° F. and watered by sprinkling. The grass species were treated with a solution containing a m-(N,N-dimethylureido)dialkylaminooxanilide 10 days after seeding; the broadleaves were treated with such a solution either 10 or 15 days after seeding, depending on the test. The plant foliage was not watered for at least three days following application of the m-(N,N-dimethylureido) dialkylaminooxanilide solution.

An example of a meta-substituted dialkylaminooxanilide solution and its application follows: 300 mg of the meta-substituted t-butyl carbanilate compound to be tested was dissolved in 45 ml of acetone. Twenty ml of this initial solution was diluted a second time with 24.5 ml of a 10:1 water and acetone mixture containing 1% Tween 20 ® (polyoxyethylene sorbitan monolaurate). This second solution was sprayed onto a seeded flat placed on a linear spray table. The solution was sprayed at a calibrated rate of 80 gallons per acre, i.e., 2 lb/A. Other rates were achieved by varying the solution concentrations and/or the rate of spray.

Injury ratings were taken two to three weeks after application of the m-(N,N-dimethylureido)-dialkylaminooxanilide solution. The effectiveness of the herbicide was determined by visual comparison of crop injury which occurred in the test flats to that which occurred in control flats.

KEY TO TABLES III, IV AND V

Compound numbers in these tables correspond to the numbers and their chemical descriptions in Table I. All rates shown are in pounds per acre. The abbreviations used to identify the species in these tables correspond to the abbreviations shown in Table II.

INJURY RATINGS

Injury to broadleaf weeds (Table III), grasses (Table IV), and crops (Table V) is shown as a percentage of damage done to the plants as compared to an evaluation of the undamaged state of the plants. The damage done to the plants is a function of the number of plants injured and the extent of injury to each plant. This rating is made two (2) weeks to three (3) weeks after application of the dialkylaminooxanilide solution.

Tables III and IV show that the meta-substituted dialkylaminooxanilide compounds tested are effective post-emergent herbicides against weed species. Table V shows that the compounds tested are selective towards cultivated crops.

TABLE III

Postemergence Control of Broadleaf Weeds

| Cmpd. No. | Rate (lb/A) | AMG | CB | JW | VL | MD | MSD | PW |
|---|---|---|---|---|---|---|---|---|
| 1 | 0.125 | 20 | 0 | 0 | 0 | 0 | 0 | 0 |
|  | 0.25 | 25 | 0 | 0 | 20 | 20 | 0 | 0 |
|  | 0.5 | 30 | 20 | 20 | 30 | 30 | 20 | 0 |
|  | 1.0 | 35 | 25 | 40 | 40 | 40 | 30 | 20 |
|  | 2.0 | 80 | — | — | 85 | 75 | — | 60 |
|  | 2.0 | 50 | 30 | 70 | 70 | 50 | 60 | 40 |
| 2 | 0.125 | 0 | 0 | 0 | 0 | 0 | 0 | 0 |
|  | 0.25 | 0 | 0 | 0 | 10 | 0 | 0 | 0 |
|  | 0.5 | 0 | 0 | 20 | 20 | 20 | 20 | 0 |
|  | 1.0 | 10 | 10 | 30 | 30 | 30 | 30 | 0 |
|  | 2.0 | 80 | — | — | 95 | 80 | — | 80 |
|  | 2.0 | 30 | 20 | 40 | 50 | 40 | 35 | 30 |
| 3 | 0.125 | 0 | 0 | 0 | 0 | 0 | 0 | 0 |
|  | 0.25 | 0 | 0 | 0 | 20 | 10 | 0 | 0 |
|  | 0.5 | 0 | 10 | 20 | 40 | 30 | 30 | 20 |
|  | 1.0 | 20 | 20 | 40 | 50 | 60 | 60 | 30 |
|  | 2.0 | 90 | — | — | 80 | 90 | — | 50 |
|  | 2.0 | 40 | 30 | 70 | 60 | 70 | 80 | 50 |
| 4 | 0.125 | 0 | 0 | 0 | 0 | 0 | 0 | 0 |
|  | 0.25 | 0 | 0 | 20 | 20 | 10 | 0 | 0 |
|  | 0.5 | 10 | 20 | 30 | 40 | 20 | 20 | 0 |
|  | 1.0 | 20 | 30 | 40 | 50 | 30 | 30 | 20 |
|  | 2.0 | 95 | — | — | 85 | 80 | — | 50 |
|  | 2.0 | 30 | 40 | 50 | 60 | 40 | 40 | 30 |
| 5 | 0.5 | 25 | 10 | 20 | 0 | 20 | 0 | 0 |
|  | 1.0 | 45 | 45 | 35 | 25 | 35 | 20 | 30 |
|  | 2.0 | 60 | — | — | 40 | 50 | — | 40 |
|  | 2.0 | 70 | 60 | 55 | 65 | 50 | 35 | 35 |
| 6 | 0.25 | 20 | 0 | 0 | 0 | 20 | 0 | 0 |
|  | 0.5 | 30 | 20 | 20 | 0 | 35 | 0 | 0 |
|  | 1.0 | 55 | 35 | 35 | 40 | 45 | 10 | 25 |
|  | 2.0 | 95 | — | — | 74 | 100 | — | 75 |
|  | 2.0 | 70 | 50 | 55 | 65 | 60 | 25 | 35 |
| 7 | 2.0 | 90 | — | — | 60 | 75 | — | 55 |
|  | 2.0 | 65 | 65 | 60 | 70 | 65 | 60 | 40 |
| 8 | 0.5 | 10 | 10 | 40 | 0 | 45 | 30 | 0 |
|  | 1.0 | 45 | 30 | 60 | 55 | 65 | 50 | 20 |
|  | 2.0 | 75 | — | — | 65 | 75 | — | 50 |
|  | 2.0 | 60 | 45 | 70 | 65 | 80 | 70 | 30 |
| 9 | 2.0 | 40 | — | — | 40 | 40 | — | 30 |
| 10 | 0.25 | 0 | 0 | 0 | 0 | 0 | 0 | 0 |
|  | 0.5 | 0 | 0 | 0 | 10 | 10 | 0 | 0 |
|  | 1.0 | 0 | 0 | 10 | 20 | 20 | 0 | 10 |
|  | 2.0 | 20 | 0 | 20 | 40 | 35 | 30 | 25 |
|  | 4.0 | 98 | — | — | 95 | 80 | — | 0 |
| 11 | 0.25 | 10 | 0 | 0 | 0 | 0 | 0 | 0 |
|  | 0.5 | 15 | 0 | 10 | 10 | 20 | 0 | 0 |
|  | 0.5 | 0 | 0 | 0 | 0 | 0 | 0 | 0 |
|  | 1.0 | 20 | 0 | 20 | 15 | 30 | 15 | 20 |
|  | 1.0 | 0 | 0 | 0 | 0 | 0 | 0 | 0 |
|  | 2.0 | 25 | 0 | 25 | 20 | 55 | 20 | 40 |
|  | 2.0 | 0 | 0 | 20 | 20 | 25 | 0 | 0 |
|  | 4.0 | 100 | — | — | 100 | 100 | — | 100 |
| 12 | 2.0 | 35 | — | — | 60 | 60 | — | 30 |
| 13 | 2.0 | 30 | — | — | 0 | 20 | — | 0 |
| 14 | 2.0 | 0 | — | — | 20 | 0 | — | 0 |
| 15 | 2.0 | 20 | — | — | 40 | 30 | — | 0 |
| 16 | 2.0 | 40 | — | — | 55 | 20 | — | 0 |

TABLE IV

Postemergence Control of Grasses

| Cmpd. No. | Rate (lb/A) | DB | FT | ARG | WG | SHC | WO | YNG |
|---|---|---|---|---|---|---|---|---|
| 1 | 0.125 | 0 | 0 | 0 | 0 | 0 | 0 |  |
|  | 0.25 | 0 | 0 | 0 | 0 | 0 | 0 |  |
|  | 0.5 | 0 | 0 | 0 | 0 | 0 | 0 |  |
|  | 1.0 | 0 | 0 | 0 | 0 | 0 | 0 |  |
|  | 2.0 | — | 20 | — | 0 | — | 0 |  |
|  | 2.0 | 0 | 20 | 20 | 20 | 0 | 0 |  |
| 2 | 0.125 | 0 | 0 | 0 | 0 | 0 | 0 |  |
|  | 0.25 | 0 | 0 | 0 | 0 | 0 | 0 |  |
|  | 0.5 | 0 | 0 | 0 | 0 | 0 | 0 |  |
|  | 1.0 | 0 | 0 | 0 | 0 | 0 | 0 |  |
|  | 2.0 | — | 10 | — | 10 | — | 0 |  |
|  | 2.0 | 0 | 10 | 20 | 20 | 0 | 10 |  |
| 3 | 0.125 | 0 | 0 | 0 | 0 | 0 | 0 |  |
|  | 0.25 | 0 | 0 | 0 | 0 | 0 | 0 |  |
|  | 0.5 | 0 | 0 | 0 | 0 | 0 | 0 |  |
|  | 1.0 | 0 | 0 | 0 | 0 | 0 | 0 |  |
|  | 2.0 | — | 0 | — | 0 | — | 0 |  |
|  | 2.0 | 0 | 0 | 0 | 0 | 0 | 0 |  |
| 4 | 0.125 | 0 | 0 | 0 | 0 | 0 | 0 |  |
|  | 0.25 | 0 | 0 | 0 | 0 | 0 | 0 |  |
|  | 0.5 | 0 | 0 | 0 | 0 | 0 | 0 |  |
|  | 1.0 | 0 | 0 | 0 | 0 | 0 | 0 |  |
|  | 2.0 | — | 20 | — | 0 | — | 20 |  |
|  | 2.0 | 0 | 0 | 0 | 0 | 0 | 0 |  |
| 5 | 0.5 | 0 | 0 | 0 | 0 | 0 | 0 | — |
|  | 1.0 | 0 | 10 | 0 | 0 | 10 | 0 | — |
|  | 2.0 | — | 0 | — | 0 | — | 0 | 0 |
|  | 2.0 | 20 | 20 | 0 | 0 | 30 | 10 | — |
| 6 | 0.25 | 0 | 0 | 0 | 0 | 0 | 0 | — |
|  | 0.5 | 0 | 0 | 0 | 0 | 0 | 0 | — |
|  | 1.0 | 10 | 10 | 0 | 0 | 20 | 0 | — |
|  | 2.0 | — | 0 | — | 0 | — | 0 | 0 |
|  | 2.0 | 25 | 20 | 20 | 10 | 35 | 0 | — |
| 7 | 2.0 | — | 25 | — | 25 | — | 20 | 20 |
|  | 2.0 | 20 | 20 | 20 | 25 | 20 | 10 | — |
| 8 | 0.5 | 0 | 0 | 0 | 0 | 10 | 0 | — |
|  | 1.0 | 10 | 20 | 0 | 20 | 20 | 10 | — |
|  | 2.0 | — | 0 | — | 0 | — | 0 | 0 |
|  | 2.0 | 20 | 30 | 10 | 30 | 35 | 20 | — |
| 9 | 2.0 | — | 0 | — | 0 | — | 0 | 0 |
| 10 | 0.25 | 0 | 0 | 0 | 0 | 0 | 0 | 0 |
|  | 0.5 | 0 | 0 | 0 | 0 | 0 | 0 | 0 |
|  | 1.0 | 0 | 0 | 0 | 0 | 0 | 0 | 0 |
|  | 2.0 | 0 | 0 | 0 | 0 | 0 | 0 | 0 |
|  | 4.0 | — | 0 | — | 0 | — | 0 | 0 |
| 11 | 0.25 | 0 | 0 | 0 | 0 | 0 | 0 | 0 |
|  | 0.5 | 0 | 0 | 0 | 0 | 0 | 0 | 0 |
|  | 0.5 | 0 | 0 | 0 | 0 | 0 | 0 | 0 |
|  | 1.0 | 0 | 0 | 0 | 0 | 0 | 0 | 0 |
|  | 1.0 | 0 | 0 | 0 | 0 | 0 | 0 | 0 |
|  | 2.0 | 0 | 0 | 0 | 0 | 0 | 0 | 0 |
|  | 2.0 | 0 | 0 | 0 | 0 | 0 | 0 | 0 |
|  | 4.0 | — | 0 | — | 0 | — | 0 | 0 |
| 12 | 2.0 | — | 0 | — | 0 | — | 0 | 0 |
| 13 | 2.0 | — | 0 | — | 0 | — | 0 | 0 |
| 14 | 2.0 | — | 0 | — | 0 | — | 0 | 0 |
| 15 | 2.0 | — | 0 | — | 0 | — | 0 | 0 |
| 16 | 2.0 | — | 0 | — | 0 | — | 0 | 0 |

TABLE V

Herbicidal Selectivity with respect to Cultivated Crops

| Cmpd. No. | Rate (lb/A) | SOY | RC | COT | CN | WH | ML |
|---|---|---|---|---|---|---|---|
| 1 | 0.125 | 0 | 0 | 20 | 0 | 0 | 0 |
|  | 0.25 | 20 | 0 | 25 | 0 | 0 | 0 |
|  | 0.5 | 30 | 0 | 30 | 0 | 0 | 0 |
|  | 1.0 | 35 | 0 | 40 | 0 | 0 | 0 |
|  | 2.0 | 70 | 40 | 60 | 0 | 0 | 0 |
| 2 | 0.125 | 10 | 0 | 10 | 0 | 0 | 0 |
|  | 0.25 | 20 | 0 | 20 | 0 | 0 | 0 |
|  | 0.5 | 25 | 0 | 25 | 0 | 0 | 0 |
|  | 1.0 | 30 | 0 | 30 | 0 | 0 | 0 |
|  | 2.0 | 35 | 20 | 35 | 0 | 0 | 0 |
| 3 | 0.125 | 0 | 0 | 20 | 0 | 0 | 0 |
|  | 0.25 | 0 | 0 | 30 | 0 | 0 | 0 |
|  | 0.5 | 20 | 0 | 35 | 0 | 0 | 0 |
|  | 1.0 | 30 | 0 | 40 | 0 | 0 | 0 |
|  | 2.0 | 50 | 30 | 45 | 0 | 0 | 0 |
| 4 | 0.125 | 0 | 0 | 0 | 0 | 0 | 0 |
|  | 0.25 | 10 | 0 | 20 | 0 | 0 | 0 |
|  | 0.5 | 20 | 0 | 30 | 0 | 0 | 0 |
|  | 1.0 | 30 | 0 | 40 | 0 | 0 | 0 |

TABLE V-continued
Herbicidal Selectivity with respect to Cultivated Crops

| Cmpd. No. | Rate (lb/A) | SOY | RC | COT | CN | WH | ML |
|---|---|---|---|---|---|---|---|
| | 2.0 | 40 | 40 | 70 | 0 | — | 20 |
| 5 | 0.5 | 30 | 0 | 15 | 0 | 0 | 0 |
| | 1.0 | 45 | 0 | 40 | 0 | 0 | 0 |
| | 2.0 | 75 | 25 | 60 | 0 | 10 | 0 |
| 6 | 0.25 | 0 | 0 | 0 | 0 | 0 | 0 |
| | 0.5 | 25 | 0 | 0 | 0 | 0 | 0 |
| | 1.0 | 45 | 25 | 25 | 0 | 0 | 0 |
| | 2.0 | 70 | 45 | 40 | 10 | 0 | 15 |
| 7 | 2.0 | 65 | 55 | 50 | 0 | 0 | 0 |
| 8 | 0.5 | 35 | 0 | 10 | 0 | 0 | 0 |
| | 1.0 | 60 | 40 | 35 | 0 | 0 | 0 |
| | 2.0 | 55 | 50 | 20 | 0 | 0 | 20 |
| 10 | 0.25 | 0 | 0 | 0 | 0 | 0 | 0 |
| | 0.5 | 0 | 0 | 0 | 0 | 0 | 0 |
| | 1.0 | 20 | 10 | 10 | 0 | 0 | 0 |
| | 2.0 | 30 | 15 | 25 | 0 | 0 | 0 |
| 11 | 0.25 | 0 | 0 | 0 | 0 | 0 | 0 |
| | 0.5 | 10 | 0 | 0 | 0 | 0 | 0 |
| | 0.5 | 20 | 0 | 0 | 0 | 0 | 0 |
| | 1.0 | 15 | 0 | 20 | 0 | 0 | 0 |
| | 1.0 | 25 | 0 | 0 | 0 | 0 | 0 |
| | 2.0 | 20 | 0 | 25 | 0 | 0 | 0 |
| | 2.0 | 30 | 0 | 0 | 0 | 0 | 0 |

Test Results

The compounds of this invention show good post-emergence control of broadleaf weeds. The compounds did not cause injury to corn, wheat and milo crops.

Formulations

A formulation is the incorporation of a formulant in a form which is directly usable on crops and weeds. As defined herein, a "formulant" is the material which is to be formulated. The formulant may be either an antidote compound alone or an herbicide and antidote composition. The purpose of the formulation is to apply the formulant to the locus where it is desired to establish herbicidal selectivity by a convenient method. The "locus" may include soil, seeds, seedlings and vegetation.

The formulations are commonly dusts, wettable powders, granules, solutions or emulsifiable concentrates.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anti-caking and anti-static agents may also be added. Dusts may be applied by spraying from boom and hand sprayers on airplanes.

Wettable powders are finely divided compositions comprising a particulate carrier impregnated with the formulant and additionally containing one or more surface active agents. The surface active agent promotes rapid dispersion of the powder in an aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omegasubstituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the formulant impregnated on a particulate inert carrier having a particle size of about 1 to 2 millimeters (mm) in diameter. The granules can be made by spraying a solution of the formulant in a volatile solvent onto the granular carrier. Examples of suitable carriers for the preparation of granules include clay, vermiculite, sawdust, and granular carbon.

Emulsifiable concentrates consist of an oil solution of the formulant plus an emulsifying agent. Prior to use the concentrate is diluted with water to form a suspended emulsion of oil droplets. The emulsifiers used are usually a mixture of anionic and nonionic surfactants. Other additives, such as suspending agents and thickeners, may be included in the emulsifiable concentrate.

When the formulant is an antidote and herbicide composition, the proportion of antidote compound to herbicide compound generally ranges from approximately 0.001 to 30 parts by weight of the antidote compound per weight of the herbicide compound.

Formulations generally contain several additives in addition to the formulant and carrier or agent. Among these are inert ingredients, diluent carriers, organic solvents, water, oil and water, water in oil emulsions, carriers of dusts and granules, and surface active wetting, dispersing and emulsifying agents. Fertilizers, e.g., ammonium nitrate, urea and superphosphate, may be included. Aids to rooting and growth, e.g., compost, manure, humus and sand, may also be included.

Alternatively, the antidote compounds and herbicide and antidote compositions of this invention can be applied to a crop by addition of the formulant to irrigation water supplied to the field to be treated. This method of application permits the penetration of the compositions into the soil as the water is absorbed.

As another alternative, the formulant can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphthalenes. Liquid solutions, like dusts, may be applied by spraying from boom and hand sprayers on airplanes.

What is claimed is:

1. A compound having the formula

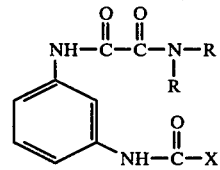

wherein
R is alkyl having 1–4 carbon atoms, inclusive; or alkenyl having 2–4 carbon atoms, inclusive; and
X is selected from the group consisting of alkyl having 1–4 carbon atoms, inclusive; cycloalkyl having 3–6 carbon atoms, inclusive; dialkylamine wherein the alkyl groups each have 1–4 carbon atoms, inclusive; and N-alkyl-N-alkoxyamine wherein the alkyl and alkoxy groups each have 1–4 carbon atoms, inclusive.

2. A compound as defined in claim 1 wherein X is dimethylamine.

3. A compound as defined in claim 2 wherein R is methyl.

4. A compound as defined in claim 2 wherein R is ethyl.

5. A compound as defined in claim 2 wherein R is n-propyl.

6. A compound as defined in claim 2 wherein R is 1-alkene.

7. A compound as defined in claim 1 wherein X is N-methyl-N-methoxyamine.

8. A compound as defined in claim 7 wherein R is ethyl.

9. A compound as defined in claim 7 wherein R is 1-alkene.

10. A compound as defined in claim 1 wherein X is ethyl.

11. A compound as defined in claim 1 wherein R is ethyl.

12. A compound as defined in claim 10 wherein R is n-propyl.

13. A compound as defined in claim 1 wherein X is cyclopropyl.

14. A compound as defined in any of claims 1, 2, 3, 4, 5, 6, 7, 8, 9, 10, 11, 12, or 13 formulated with an inert diluent carrier or agent.

15. A method of post-emergent weed pest control comprising:

applying to the locus where control is desired an herbicidally effective amount of a compound of the formula

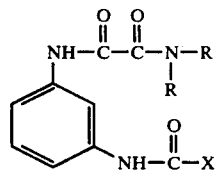

wherein

R is alkyl having 1-4 carbon atoms, inclusive; or alkenyl having 2-4 carbon atoms, inclusive; and X is selected from the group consisting of alkyl having 1-4 carbon atoms, inclusive; cycloalkyl having 3-6 carbon atoms, inclusive; dialkylamine wherein the alkyl groups each have 1-4 carbon atoms, inclusive; and N-alkyl-N-alkoxyamine wherein the alkyl and alkoxy groups each have 1-4 carbon atoms, inclusive.

16. A method as defined in claim 15 wherein X is dimethylamine.

17. A method as defined in claim 16 wherein R is methyl.

18. A method as defined in claim 16 wherein R is ethyl.

19. A method as defined in claim 16 wherein R is n-propyl.

20. A method as defined in claim 16 wherein R is 1-alkene.

21. A method as defined in claim 15 wherein X is N-methyl-N-methoxyamine.

22. A method as defined in claim 21 wherein R is ethyl.

23. A method as defined in claim 21 wherein R is 1-alkene.

24. A method as defined in claim 15 wherein X is ethyl.

25. A method as defined in claim 16 wherein R is ethyl.

26. A method as defined in claim 25 wherein R is n-propyl.

27. A method as defined in claim 15 wherein X is cyclopropyl.

* * * * *

UNITED STATES PATENT AND TRADEMARK OFFICE
CERTIFICATE OF CORRECTION

PATENT NO. : 4,406,692
DATED : September 27, 1983
INVENTOR(S) : Rayman Y. Wong

It is certified that error appears in the above-identified patent and that said Letters Patent is hereby corrected as shown below:

In the Abstract, after the word "formula" and before the word "wherein" please insert the following formula:

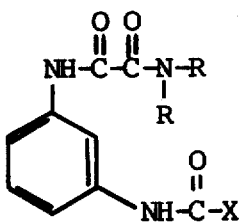

In the Abstract, line 1, delete "t,10".

Signed and Sealed this

Twenty-sixth Day of August 1986

[SEAL]

Attest:

DONALD J. QUIGG

Attesting Officer

Commissioner of Patents and Trademarks